United States Patent [19]

Phalangas et al.

[11] Patent Number: 4,950,467
[45] Date of Patent: Aug. 21, 1990

[54] ULTRAVIOLET RADIATION ABSORBING COMPOSITIONS

[75] Inventors: Charalambos J. Phalangas; Alfred J. Restaino; Lau S. Yang, all of Wilmington, Del.

[73] Assignee: ICI Americas Inc., Wilmington, Del.

[21] Appl. No.: 930,523

[22] Filed: Nov. 14, 1986

[51] Int. Cl.$^5$ .................. A61K 7/40; A61K 7/42; A61K 7/44; A61K 31/74

[52] U.S. Cl. .................. 424/59; 106/3; 106/6; 424/47; 424/60; 424/61; 424/63; 424/64; 424/70; 424/74; 424/78; 424/80; 424/81; 514/839; 514/844; 514/845; 514/847; 514/880; 514/937; 514/939

[58] Field of Search .................. 424/59, 60

[56] References Cited

U.S. PATENT DOCUMENTS

| | | | |
|---|---|---|---|
| 3,052,636 | 9/1962 | Stroebel et al. | 424/59 |
| 3,065,144 | 11/1962 | Kreps et al. | 424/59 |
| 3,201,406 | 8/1965 | Moffet | 424/59 |
| 3,215,550 | 11/1965 | Stroebel et al. | 424/59 |
| 3,215,724 | 11/1965 | Stroebel et al. | 424/59 |
| 3,215,725 | 11/1965 | Stroebel et al. | 424/59 |
| 3,256,312 | 6/1966 | Stroebel et al. | 424/59 |
| 3,270,045 | 8/1966 | Stroebel et al. | 424/59 |
| 3,272,810 | 9/1966 | Stroebel et al. | 424/59 |
| 3,275,520 | 9/1966 | Stroebel et al. | 424/59 |
| 3,311,636 | 3/1967 | Moffet | 424/59 |
| 3,336,357 | 8/1967 | Stroebel et al. | 424/59 |
| 3,381,006 | 4/1968 | Suh | 424/59 |
| 3,506,758 | 4/1970 | Epstein et al. | 424/59 |
| 3,644,614 | 2/1972 | Streschnak et al. | 424/59 |
| 3,751,563 | 8/1973 | Richardson | 424/59 |
| 4,108,880 | 8/1978 | Gander et al. | 424/59 |
| 4,457,911 | 7/1984 | Conner et al. | 424/59 |
| 4,515,774 | 5/1985 | Conner et al. | 424/59 |

OTHER PUBLICATIONS

Kupriyanova et al, 1970, vol. 73, p. 7091w, Chem. Abs.
Martelli et al, 1973, vol. 78, p. 135492t, Chem. Abs.
Lechat et al, 1981, vol. 95, p. 124443c, Chem. Abs.
Tomazic et al, 1982, vol. 96, p. 122245m, Chem. Abs.
DeSa, 1982, vol. 96, p. 34120m, Chem. Abs.
Martelli et al, 1978, vol. 89, p. 43222d, Chem. Abs.
Brunke, 1983, vol. 99, p. 128162r, Chem. Abs.
Gokaran et al, 1970, vol. 73, p. 7092, Chem. Abs.

Primary Examiner—Dale R. Ore

[57] ABSTRACT

Sunscreen compositions are described which contain certain 5-phenylpentadienoate esters which act as UV filters when incorporated in a carrier in amounts ranging from 0.1–50% by weight.

9 Claims, No Drawings

ULTRAVIOLET RADIATION ABSORBING COMPOSITIONS

The present invention is directed to ultraviolet absorbing compositions comprising substituted 5-phenylpentadienoate esters and blends thereof which are useful as protective coatings and to a method for protecting substrates against the harmful effects of actinic radiation. It is further directed to a process for making ultraviolet absorbing coating compositions.

Ultraviolet radiation absorbing coatings are useful in protecting substrates such as plastic resins against accelerated deterioration and the skin of warm blooded animals against severe erythema edema and blistering. The compositions of the invention are generally referred to as sunscreen compositions and blends thereof can be incorporated with waxes, oils, lacquers, soft resins in the preparation of furniture and auto polishes, cosmetics, suntan oils and lotions, lipstick, hair treatments, skin formulations, contact lenses, and window washing solutions, etc. In particular, the invention relates to sunscreen compositions comprising an acceptable carrier having incorporated therein an effective amount of a filtering agent for ultraviolet radiation selected from a compound of formula I (see Table of Formulas below) wherein $R^1$ is selected from an alkyl, alkenyl, alkynyl, aromatic and alkyl substituted aromatic group having 1 to 22 carbon atoms including straight and branched chain arrangements including ethylenic unsaturation, monohydroxy and monoalkoxy substitution;

$R^2$ may be selected from H, $R^1$, —CN, or aryl;

$R^3$, $R^4$, $R^5$ may be selected from —H or $R^1$;

$R^6$, $R^7$, $R^8$, $R^9$, $R^{10}$ are independently selected from —H, alkyl groups having 1–10 carbon atoms either straight chain or branched, and no more than one $OR^{11}$ group wherein $R^{11}$ is an alkyl group having 1 to 10 carbon atoms either straight or branched chain;

$R^8$ can also be —N$(R^{12})_2$ wherein $R^{12}$ is —H or $R^{11}$, —$COR^{11}$; or —$COCH_2COR^{11}$ and including compounds wherein $R^6$, $R^7$, $R^8$, $R^9$, $R^{10}$ may be a hydroxyl group or a substituted benzyl group of general formula II wherein $Y^1$ and $Y^2$ may be hydrogen, hydroxy or methoxy.

Of particular interest are compositions which provide selective absorption of actinic radiation in the 290–320 nm range as well as the 320–400 nm range of wavelength. The compounds may be present in the coating compositions as a fine divided solid or as a solute dispersed in a pharmaceutically acceptable carrier when applied to a surface such that the selection of said carrier in the coating composition permits absorbency in the 290–400 nm range.

The compositions of the invention comprise the compounds in amounts needed to provide protection against the harmful effects of ultraviolet radiation. The amount or concentration of the compounds in the composition is such that when the composition is topically applied the desired protection is provided. The amount needed to provide the desired protection can vary with the characteristics of the compound i.e. its extinction coefficient or substantively, the nature of the carrier, the source and intensity of the radiation and other well recognized variables. Suitable amounts can be readily determined by standard methods of testing. Preferably the UV filter compounds are incorporated in the carrier in an amount ranging from about 0.1% to about 50% by weight and usually in amounts of 1.0–15% by weight and preferred 0.5%–30% by weight.

Acceptable carriers include any vehicle or medium capable of incorporating the UV filter compound in a manner permitting uniform topical application. The term "pharmaceutically acceptable" is intended as a term of qualification in that the carrier should be dermatologically innocuous to warm blooded animals and cosmetically acceptable. The carrier may comprise a wax, oil or cream base material in which the agent can be held in a clear solution or a uniform dispersion, for example, as submicron size particles. Preferably the carrier comprises a suitable solvent or a mixture of solvents capable of dissolving the UV filter compounds to provide a concentration that is effective as a sunscreen agent when incorporated in the sunscreen formulation. Solvents which may be useful include alcohols, ketones, esters, polyesters such as oils, hydrocarbons, chlorinated hydrocarbons, ethers, polyethers, polyetherpolyols and other special solvents such as dimethylsulfoxide, dimethylformamide and the like. Such solvents are considered useful only if they do not permanently interact with the active filtering agents of the invention to shift the total effective absorption outside of the 290–400 nm range.

The sunscreening compositions may be applied as a clear liquid or a lotion comprising a water-in-oil, or oil-in-water or a multiple emulsion. Either the oil or water base or both may be used as a carrier for the sunscreening compositions of the invention. The oil base material and the water and oil base compositions will form a continuous film of the UV filtering compound. Such films also provide long lasting protection against sun induced erythema. Sunscreening formulations are generally used in hot weather and at beaches where people enjoy bathing activities. It is therefore essential that the protective coating applied to the skin is not appreciably affected by water or perspiration. The compositions herein disclosed are included in a thin layer protective coating on the skin of warm blooded animals and provide long lasting protection against erythema and do not appreciably decompose over practical periods of exposure to sunlight.

The 5-phenyl-2,4-pentadienoate esters are conveniently made as condensation products of cinnamaldehyde derivatives with various substituted acids, anhydrides and esters.

The following preparative examples serve as nonlimiting illustrations of the types of compounds included in the invention and all parts and percentages are expressed on a weight basis unless otherwise specified.

PREPARATION 1

2-Methyl-5-phenyl-2,4-pentadienoic acid ($R^1$=H, $R^2$=Methyl, $R^3$–$R^{10}$=H)

In a 3 liter round bottom flask equipped with a mechanical stirrer, a thermometer and a condenser were added trans-cinnamaldehyde (3696 g, 3 mols), propionic anhydride (429 g, 3.3 mols) and sodium propionate (306 g, 3.75 mols). The mixture was heated to 160° C. for 3 hours, and then poured into 3 liters of ice water. The solid was collected and washed with 500 ml of 1% $H_2SO_4$ and twice with water. The dried product weight 614 g. This crude product can be used to prepared the esters without further purification. Else, the product can be recrystallize from toluene to give a light yellow solid m.p. 165° C.

PREPARATION 2

Ethyl 2-methyl-5-phenyl-2,4-pentadienoate ($R^1$=ethyl, $R^2$=methyl, $R^3$-$R^{10}$=H)

To the crude 2-methyl-5-phenyl-2,4-pentadienoic acid (514 g), prepared according to the procedure described in Preparation 1, were added pure ethanol (412 ml), toluene (550 ml) and conc. sulfuric acid (41 ml). The mixture was heated under reflux (85° C.) for 20 hours. The aqueous layer separated and the organic layer was washed once with water and twice with saturated sodium bicarbonate solution. After drying over sodium sulfate, the solvent was removed. The residue was distilled to yield the ethyl ester (432 g, 67% overall yield from cinnamaldehyde): b.p. 125° C./1 mm Hg. $\lambda$max=313 nm.

PREPARATION 3

2-Ethylhexyl-2-methyl-5-phenyl-2,4-pentadienoate ($R^1$=2-ethyl hexyl, $R^2$=methyl, $R^3$-$R^{10}$=H)

In a one liter flask equipped with a thermometer and a Dean-Stark water trap, were added the crude 2-methyl-5-phenyl-2,4-pentadienoic acid (205 g prepared from 1 mol of cinnamaldehyde according to the procedure described in Preparation 1), 2-ethyl hexanol (200 g), toluene (100 ml) and toluene sulfonic acid (4 g). The mixture was heated under reflux until 18 ml of water was collected. The mixture was washed with saturated sodium bicarbonate solution and then water. After the removal of the solvent, the product was distilled to yield 232 g of the 2-ethylhexyl ester (b.p. 177° C./0.7 mm Hg).

PREPARATION 4

2-Hydroxyethyl-2-methyl-5-phenyl-2,4-pentadienoate ($R^1$=2-hydroxyethyl, $R^2$=methyl, $R^3$-$R^{10}$=H)

To a suspension of the recrystallized 2-methyl-5-phenyl-2,4-pentadienoic acid (5 g prepared according to the procedure described in Preparation 1) in 50 ml of methylene chloride and 0.2 ml of dimethyl formamide was added thionyl chloride (3.8 g). The mixture was stirred for 30 minutes and then poured into a mixture of ethanol (50 ml) and sodium carbonate (5 g). After another 30 minutes, the reaction mixture was washed with water and dried over sodium sulfate. The solvent was evaporated to give the hydroxyethyl ester (5 g, 97% pure by G.C.) $\lambda$max=311 nm.

PREPARATION 5

Ethylene Glycol Di(2-methyl-5-phenyl-2,4-pentadienoate) ($R^1$=$C_2H_4$-Formula I; $R^2$=Methyl, $R^3$-$R^{10}$=H)

To a suspension of recrystallized 2-methyl-5-phenyl-2,4-pentadienoic acid (5 g, prepared according to that of Preparation 1) in 50 ml of methylene chloride and 0.5 ml of dimethyl formamide was added thionyl chloride (3.5 g). The mixture was stirred for 30 minutes. To this solution were added 8 g of pyridine and 0.84 g of ethylene glycol. The reaction mixture was stirred for 30 minutes and then washed with water and dried over sodium sulfate. The solid product was recrystallized twice from toluene to give the diester (0.5 g): m.p. 152° C. $\lambda$max=313 nm.

PREPARATION 6

(2-Hydroxypropyl)-2-methyl-5-phenyl-2,4-pentadienoate ($R^1$=2-hydroxypropyl, $R^2$=Methyl, $R^3$-$R^{10}$=H)

To a suspension of the recrystallized 2-methyl-5-phenyl-2,4-pentadienoic acid (16 g, prepared according to the procedure described in Preparation 1) in 160 ml of methylene chloride and 1 ml of dimethyl formamide was added thionyl chloride (11.1 g). The mixture was stirred for 30 minutes and then poured into a mixture of propylene glycol (130 g) and sodium carbonate (20 g). After another 30 minutes, the reaction mixture was washed with water and dried over sodium sulfate. The solvent was removed to yield 19.2 g of the crude hydroxy propyl ester (97% pure by G.C.). $\lambda$max=313 nm.

PREPARATION 7

1,2-Propylene Glycol Di(2-methyl-5-phenyl-2,4-pentadienoate) ($R^1$=—$CH_2C(CH_3)$O-Formula I, $R^2$=Methyl, $R^3$-$R^{10}$=H)

To a suspension of the recrystallized 2-methyl-5-phenyl-2,4-pentadienoic acid (10 g, prepared according to the procedure described in Preparation 1) in 100 ml of methylene chloride and 1 ml of dimethyl formamide was added thionyl chloride (7.0 g). The mixture was stirred for 30 minutes. To this solution were added 15 g of pyridine and 2 g of propylene glycol. The mixture was stirred for another 30 minutes. The solution was then washed with water and dried over sodium sulfate. After the removal of the solvent, the residue was recrystallized from hexane to give a white solid (7 g), identified as the diester. $\lambda$max=313 nm.

PREPARATION 8

2-Ethyl-5-phenyl-2,4-pentadienoic acid ($R^1$=H, $R^2$=Ethyl, $R^3$-$R^{10}$=H.)

In a one liter flask were added trans-cinnamaldehyde (66 g), sodium butyrate (69 g) and butyric anhydride (95 g). The mixture was heated to 160° C. for 4 hours and then poured ice water (1 liter) to give the crude product (107 g). The product can be further purified by recrystallization from toluene, m.p. 143° C.

PREPARATION 9

Ethyl 2-ethyl-5-phenyl-2,4-pentadienoate ($R^1$=ethyl, $R^2$=ethyl, $R^3$-$R^{10}$=H)

To a suspension of the recrystallized 2-ethyl-5-phenyl-2,4-pentadienoic acid (10 g, prepared according to the procedures described in Preparation 8) in 100 ml of methylene chloride and 1 ml of dimethyl formamide was added thionyl chloride (7.2 g). The mixture was stirred for 30 minutes and poured into a mixture of ethanol (100 ml) and sodium carbonate (10 g). After another 30 minutes, the mixture was washed with water and dried over sodium sulfate. After the removal of the solvent, the residue was distilled to give the ester (11 g) as colorless liquid; b.p. 135° C./0.5 mm Hg. $\lambda$max=313 nm.

PREPARATION 10

Ethyl 3-methyl-5-phenyl-2,4-pentadienoate ($R^1$=ethyl, $R^2$=H, $R^3$=methyl, $R^4$-$R^{10}$=H)

To 36 g of zinc (20 mesh), 3 g of copper powder, and 50 ml of toluene was added a solution of benzal acetone (73 g), ethyl bromoacetate (92 g) in 250 ml of toluene.

The mixture was refluxed for 30 minutes, cooled, and 200 ml of 20% acetic acid was added. The organic layer was separated and washed with water, and dried over sodium sulfate. The solution was then placed in a flask equipped with a Dean-Stark trap and heated to reflux in the presence of 2.5 g of toluene sulfonic acid until 7 ml of water was collected. After the removal of toluene, the residue was distilled to give the ester (20 g, b.p. 140° C./2 mm Hg). λmax=308 nm.

PREPARATION 11

Ethyl 2,5-Diphenyl-2,4-pentadienoate ($R^1$=ethyl, $R^2$=$C_6H_5$, $R^3$-$R^{10}$=H.)

In a 1 liter flask was added a mixture of cinnamaldehyde (66 g), acetic anhydride (127.5 g), phenyl acetic acid (68 g) and triethyl amine (50.5 g). The mixture was heated to 140° C. for 4 hrs. and then poured into one liter of ice water. The solid was collected and dried to afford the acid. This crude acid was esterified with ethanol according to a procedure similar to that described in Preparation 2. The product was distilled to yield 60 g of the ethyl ester (43%), b.p. 157° C./0.15 mm Hg. λmax=325 nm.

PREPARATION 12

Ethyl 2-ethyl-5-phenyl-2,4-pentadienoate ($R^1$+$R^2$=Ethyl, $R^3$-$R^{10}$=H)

In a 250 ml three necked flask was placed 53.2 g 2-ethyl-5-phenyl-2,4-pentadienoic acid (prepared according to Preparation 8) in 200 ml absolute ethanol. To this was added 5 ml sulfuric acid and the contents were heated to reflux for 20 hours. The excess ethanol was removed by distillation under reduced pressure and the residue dissolved in ether, washed with 50 ml $H_2O$, 50 ml 5% $NaHCO_3$, and 50 ml $H_2O$. The ehter layer was dried over $MgSO_4$ and the ether removed by rotary evaporation. Distillation of the resulting liquid gave 53.5 g of pure ethyl ester (BP 135° C. at 0.5 mm Hg).

PREPARATION 13

2-Cyano-5-phenyl-2,4-pentadienoic acid ($R^1$=H, $R^2$=—CN, $R^3$-$R^{10}$=H)

To a solution of cyano acetic acid in 200 ml of 10% aqueous potassium hydroxide was added trans-cinnamaldehyde (26 g). The mixture was stirred at 35° C. for 2 hrs. and acidified with 100 ml of conc. hydrochloric acid. The solid was collected and washed to yield 2-cyano-5-phenyl-2,4-pentadienoic acid (36 g, 90% yield), m.p. 196° C. Recrystallized from ethanol yielded pure product, m.p. 211° C.

PREPARATION 14

(2-Ethyl)hexyl 2-cyano-5-phenyl-2,4-pentadienoate ($R^1$=(2-ethyl)hexyl, $R^2$=—CN, $R^3$-$R^{10}$=H)

To 56 g of 2-cyano-5-phenyl-2,4-pentadienoci acid, prepared according to the procedure of Preparation 13, was added a solution of 100 g of 2-ethyl hexanol, and 5 g of toluene sulfonic acid in 250 ml of toluene. The mixture was heated under reflux until 6 ml of water was collected. The solution was washed with water and dried over sodium sulfate. The solvent was evaporated to yield the crude product. Recrystallization from hexane give the ethyl hexyl ester as a light yellow solid (52 g) m.p. 82° C. λmax=344 mn.

PREPARATION 15

Isoamyl 2-Cyano-5-phenyl-2,4-pentadienoate ($R^1$=isoamyl, $R^2$=—CN, $R^3$-$R^{10}$=H)

To a suspension of 2-cyano-5-phenyl-2,4-pentadienoic acid (219 g, prepared according to the example of Preparation 13) in 1 liter of toluene was added 116 g technical grade isoamyl alcohol (mixture of 2 and 3 methyl isomers). To this mixture was added 10 ml sulfuric acid. The reaction was heated to reflux and the water collected in a Dean Stark trap. After three hours, the reaction was cooled, washed with 300 ml water, 300 ml 5% $NaHCO_3$ and finally with 300 ml water. The toluene layer was dried over magnesium sulfate and removed by rotary evaporation. The crude product was recyrstalized twice from 95% ethanol to yield the ester as a yellow solid. (mp 77° C.).

PREPARATION 16

Ethyl 2-cyano-5-phenyl-2,4-pentadienoate ($R^1$=Ethyl, $R^2$=—CN, $R^3$-$R^{10}$=H)

To a suspension of 2-cyano-5-phenyl-2,4-pentadienoic acid (26.8 g) in 300 ml of methylene chloride and 15 ml of dimethyl formamide was added thionyl chloride (19.2 g). The mixture was stirred for one hour and poured into a mixture of ethanol (200 ml) and sodium carbonate (20 g). The reaction mixture was washed with water and the solvent was evaporate. The crude product was recrystallized from hexane-toluene (1:1) to give the ethyl ester, m.p. 105° C. λmax=343 nm.

PREPARATION 17

Ethyl 2,4-dimethyl-5-phenyl-2,4-pentadienoate ($R^1$=ethyl, $R^2$ and $R^4$=methyl, $R^3$, $R^5$-$R^{10}$=H)

To a mixture of sodium propionate (40 g) and propionic anhydride (67 g) was added 2-methyl-cinnamaldehyde (50 g). The mixture was heated to 160° C. for 4 hours, and poured into ice water. The solid was collected (75 g). Recrystallization twice from hexane give 2,4-dimethyl-5-2,4-pentadienoic acid as colorless needles, m.p. 96°-97° C.

To 10 g of the acid in 100 ml of methylene chloride and 1 ml of dimethyl formamide was added thionyl chlorine (7.1 g). The mixture was stirred for one hour and poured into ethanol (100 ml) containing sodium carbonate (15 g). After another hour, the mixture was washed with water. The solvent was evaporated and the residue distilled to yield the ethyl ester as colorless liquid (10.2 g, 90% yield), b.p. 130° C./0.5 mm Hg. λmax=301 nm.

PREPARATION 18

2-Methyl-5-(p-methoxy phenyl)-2,4-pentadienoic acid and its ethyl ester ($R^1$=ethyl, $R^2$=methyl, $R^8$=—$OCH_3$, $R^3$-$R^7$, $R^{9-10}$=H)

To a mixture of propionic anhydride (18 g) and sodium propionate (10.7 g) was added p-methoxy cinnamaldehyde (15 g, prepared from p-anisaldehyde and acetaldehyde). The mixture was heated to 160° C. for 4 hours, and then poured into ice water to give the crude acid (10.5 g). To a suspension of this acid (5 g) in 50 ml of methylene chloride and 1 ml of dimethyl formamide was added thionyl chloride (3.3 g). The mixture was stirred for 15 minutes and then poured into 200 ml of ethanol containing 10 g of sodium carbonate. After washing with water the solvent was removed and the residue was distilled to yield the ester (1.5 g), b.p. 125° C./0.2 mm Hg. λmax=334 nm.

PREPARATION 19

Ethyl 5-phenyl-2,4-pentadienoate ($R^1$=ethyl, $R^2$=H)

Into a one liter round bottom flask equipped with a stirrer, condenser, thermometer and heating mantle, 198 grams (1.5 mols) of cinnamaldehyde, 230 grams (2.25 mols) of acetic anhydride, 25 grams (0.25 mols) potassium acetate, and 49 grams (0.60 mols) of sodium acetate were charged. The contents were brought up to 145° C. and maintained at 145°-150° C. for ninety minutes. Approximately 100 ml of acetic acid/acetic anhydride were stripped off leaving a red brown slurry. The resultant slurry was cooled to room temperature and the solids filtered off and rinsed with acetone. The dry filtercake (185 grams) was dissolved in two liters of 5% potassium carbonate solution at 65° C. Addition of 100 ml of 37.8% HCl to this solution yielded 5-phenyl-2,4-pentadienoic acid as a light yellow precipitate. The precipitate was filtered and dried. The dried acid was esterified with ethanol in the presence of sulfuric acid. The resultant ethyl 5-phenyl-2,4-pentadienoate was purified by vacuum distillation. The pure product was found to have a max of 309 nm, and an extinction coefficient of 35,500.

PREPARATION 20

Ethyl 2-butyl-5-phenyl-2,4-pentadienoate $R^1$=ethyl, $R^2$=n-butyl; $R^3$-$R^{10}$=H In a 500 ml three necked flask was placed 7.0 g Zn dust and 0.7 g Cu powder in 150 ml dry toluene. To this suspension was added a solution of 13.2 g (0.1 mol) cinnamaldehyde and 22.3 g (0.1 mol) ethyl 2-bromohexanoate in 100 ml toluene. The reaction was refluxed overnight under nitrogen, cooled to room temperature and washed two times with 140 ml of 20% acetic acid and two times with 150 ml water. The organic phase was dried over magnesium sulfate and the solvent removed by rotary evaporation. Distillation of the crude product (24.9 g) resulted in isolation of 10.0 g ethyl 2-butyl-5-phenyl-pentadienoate. BP: 135-138 @ 0.1 mm Hg UV ($CH_2Cl_2$): λmax 315, ε=33,280, K=129.

PREPARATION 21

Ethyl 2-cyano-5(4-tert-butylphenyl)-2,4-pentadienoate $R^1$=ethyl; $R^2$=—CN; $R^8$=t-butyl, $R^3$-$R^6$, $R^9$, $R^{10}$=H To a solution of 2.7 g (32 mmol) cyanoacetic acid in 50 ml 10% KOH solution was added 6.0 g (32 mmol) of 4-tert-butylcinnamaldehyde. The reaction was stirred overnight at room temperature, acidified to pH 3 with HCl and the resulting solids isolated by filtration. The dried solids were dissolved in 75 ml methylenen chloride containing 0.5 g DMF. This solution was treated with 9.5 g (80 mmol) $SOCl_2$ and refluxed for 3 hours. After evaporation of the volatiles by rotary evaporation, the residue was poured into 100 ml ethanol containing 5 g sodium carbonate. This suspension was stirred 30 minutes and then poured into 500 ml water, extracted two times with 150 ml $CH_2Cl_2$ and dried over magnesium sulfate. After stripping of the solvent, the residue was chromatographed, yielding 5.0 g ethyl 2-cyano-5-(4-tert-butylphenyl)-2,4-pentadienoate as a yellow oil which crystallized on standing. MP 65°-70° C., UV ($CH_2Cl_2$), λmax 358, ε=39903, K=141.

PREPARATION 21

Amyl 2-cyano-5-phenyl-2,4-pentadienoate $R^1$=n-amyl; $R^2$=—CN; $R^3$-$R^{10}$=H In a 500 ml three necked flask was placed 10.0 g (50 mmol) 2-cyano-5-phenyl-2,4-pentadienoic acid in 150 ml toluene. To this suspension was added 37 g (0.5 mol) of an 8:2 mixture of 3-methyl-1-butanol/2-methyl-1-butanol. After addition of 2.0 g p-toluenesulfonic acid, the misture was refluxed for 5.5 hours while collecting the water in a Dean-Stark trap. The mixture was then washed two times with 150 ml of 5% $NaHCO_3$, two times with 5% water. After drying and stripping of the solvent, the residue was recrystallized from ethanol, yielding 9.1 g (71%) "amyl" 2-cyano-5-phenyl-pentadienoate as a light yellow solid. MP 75-76 C. UV ($CH_2Cl_2$) λmax 342, ε=36200, K=142.

It has been established that actinic the radiation between 290 nm and 320 nm produces substantially all the burning or erythemal energy and a substantial portion of the tanning energy, while the radiation between 320 nm and 400 nm produces incident tanning. The cosmetic industry has divided these spectra into the burning range UV-B (290-320 nm) and the tanning range UV-A (320-400 nm). Since approximately 76% of the physiological tanning potential of sunlight is found in the UV-B range and the balance is found in the UV-A range, it is desireable to have a substantial amount of the radiation in those ranges filtered out before it produces a harmful effect on the surface of human skin. While sunscreen lotions have been formulated to be most effective in the UV-B range more recent studies have indicated that it is desireable to have collective adsorption in the UV-A range as well. It has been difficult to find a practical compound which effectively adsorbs in bath ranges. Therefore, formulators must resort to the combination of two compounds which are each effective either in the UV-B, or UV-A range to provide maximum skin protection. No single compound falling within the definition of formula I is effective over the entire 290-400 nm range and therefore two or more compounds can be selected and blended within the formulation at varying concentrations at the desired balance between burning and tanning is accommodated. Such a combination is shown in Example 13. It is preferred to have a formulation having at least one compound which absorbs in the 290-320 nm range and at least one other which absorbs in the 320-400 nm range. At least one can be selected from formula I.

The use of the UV filters of the invention can be demonstrated in lotion formulations which are topically applied to the surface of the skin. The effectiveness of the UV light absorbers are tested on human subjects by treating a 1 cm square section of a subjects' back with predetermined amounts of lotion, exposing the treated areas to UV light for a set period of time and thereafter making a visual comparison with untreated and fully masked skin areas. The SPF (skin protection factor) is calculated by comparing the effects of radiation on protected skin with the unprotected skin.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1–4 and controls A and B all ingredients can be mixed together and stirred in conventional apparatus. Since in many cases a single compound used at a reasonable concentration does not effectively protect throughout the whole region of the earth reaching solar UV spectrum, blends of two or more UV absorbers can be used in a formulation to afford greater protection. To illustrate the effectiveness of the compounds of the invention in sunscreen formulations Preparation 9 was formulated into creams and lotions for extensive testing. The formulations are shown in Tables 1 and 2.

TABLE 1
Sunscreen Formula

| Ingredient | Examples (% by Weight) | | |
|---|---|---|---|
| | 1 | 2 | Control A |
| Preparation No. 9 | 2 | 8 | 0 |
| Mineral Oil | 5 | 5 | 5 |
| Stearyl Alcohol | .5 | .5 | .5 |
| Polyoxyethylene (21)steryl ether | 2 | 2 | 2 |
| Polyoxyethylene (2)stearyl ether | 2 | 2 | 2 |
| Silicone Oil | .5 | .5 | .5 |
| Water (deionized) | 87.5 | 81.5 | 89.5 |
| Carbopol ® 940 | .2 | .2 | .2 |
| Sodium Hydroxide (10%) | .2 | .2 | .2 |
| Dowicil ® 200 | .1 | .1 | .1 |
| Physical Form | cream | lotion | cream |

TABLE 2
Sunscreen Formula

| Ingredient | Examples (% by Weight) | | |
|---|---|---|---|
| | 3 | 4 | Control B |
| Preparation No. 9 | 2 | 8 | 0 |
| Petrolatum (Snow White USP) | 35 | 35 | 35 |
| Polyoxyethylene (21)stearyl ether | 1.16 | 1.16 | 1.16 |
| Polyoxyethylene (2)stearyl ether | 3.86 | 3.86 | 3.86 |
| Silicone Oil | 3 | 3 | 3 |
| Water (deionized) | 54.08 | 48.08 | 56.08 |
| Carbopol ® 934 | 0.4 | 0.4 | 0.4 |
| Sodium Hydroxide (10%) | 0.4 | 0.4 | 0.4 |
| Dowicil ® 200 | 0.1 | 0.1 | 0.1 |
| Physical Form | cream | cream | cream |

Examples 1–4 were tested on ten female subjects ranging from ages 27–50 having skin type I (always burns easily, never tans), type II (always burns easily, tans minimally) and type III (burns moderately, tans gradually). Each subject was exposed to UV radiation on 3 separate days at 27, 28 and 29 (mW/cm$^2$) respectively. Templates were applied to individual skin sites on designated areas of the back. Application of the test material was made by uniformly spreading the lotion or cream over a 50 cm$^2$ area (3.5 cm by 14.3 cm) at a dose of 2 mg/cm$^2$ with a finger cot. Approximately 15 minutes after application the sites were irradiated. Test sites were scored approximately 24 hours after exposure.

The minimum erythema dose (MED) for each treatment and each subject was determined and compared with the MED for unprotected skin. The SPF was determined for each example by the following formula SPF=[MED (protected skin)/MED (unprotected skin)]. Results of the tests appear in Table 3.

TABLE 3

| Sunscreen Formula | |
|---|---|
| Ex. No. | SPF (mean) |
| Control A | 1.42 |
| 1 | 4.38 |
| 2 | 5.55 |
| Control B | 1.29 |
| 3 | 5.08 |
| 4 | 9.20 |

In addition to their use in coating skin surfaces to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and may be used singly or in combination to provide a winder range of protection. The following formulations are given to demonstrate a few of the many aplications.

Example No. 5
Aerosol Hairdressing

| Filtering Agent | Carrier Ingredients | Composition (% by Wt.) |
|---|---|---|
| Prep 4 | | 5.0 |
| | Decaglycerol monolaurate | 2.0 |
| | Polypropylene (200) monooleate | 3.0 |
| | Ethoxylated (10) lanolin alcohols | 1.0 |
| | Propylene glycol | 2.0 |
| | Ethyl alcohol, anhydrous | 39.5 |
| | Protein polypeptide (20% alcoholic) | 1.2 |
| | Isopropyl myristate | 1.3 |
| | Propellant 11 | 15.0 |
| | Propellant 12 | 30.0 |
| | Water | q.s. |

Procedure for Formula: Dissolve all ingredients in slightly warmed ethylalcohol, avoiding loss of the alcohol, add the water, and agitate well to disperse any haze. Filter the concentrate and fill into aerosol containers. Add propellants.

Example No. 6
Formula for Creamy Type Lipstick Base

| Filtering Agent | Carrier Ingredients | Composition (% by Wt.) |
|---|---|---|
| Prep 11 | | 5 |
| | Carnauba wax | 3 |
| | Candelilla wax | 7 |
| | Ozokerite | 3 |
| | Beeswax | 7 |
| | Lanolin | 10 |
| | Castor oil | 60 |
| | Isopropyl myristate | 5 |
| | Perfume | q.s. |

Example No. 7
Water-In-Oil (W/O), Detergent Resistant, Liquid Auto Polish

| Filtering Agent | Carrier Ingredients | Composition (% by Wt.) |
|---|---|---|
| Part A | 2.00% Durmont 500 Montan Wax | (Dura Commodities) |
| Part B | 0.75% DC 530 Silicone Fluid 4.25% DC 531 Silicone Fluid 1.50% SPAN ® 80 10.00% Kerosene | (Dow Corning) |

-continued

| | | | |
|---|---|---|---|
| | 16.50% Stoddard Solvent | | |
| | 5.0% Preparation 5 | | |
| Part C | 10.00% Kaopolite SFO | (Kaopolite) | |
| Part D | 50.00% Water | | |

Method of Preparation:
1. Melt wax in Part A (85–90° C.)
2. Add Part B ingredients to melted wax and stir to blend well. Return temperature to 85–90° C.
3. Add Part C to Part A/Part B blend and mix until uniform with medium agitation. Keep temperature in the 85–90° C. range.
4. Heat Part D to 95° C. and slowly add to the blend with high speed stirring until emulsion is obtained.
5. Cool to 40–45° C. with continuous stirring.
6. Homogenize.

Example No. 8
Neutral Base Lacquer

| Materials | Pounds |
|---|---|
| Urethane 60% N.V. | 32 |
| Long oil alkyd 60% N.V. | 352 |
| Triton X-45 | 7.5 |
| Nuxtra Calcium 6% | 12 |
| Bentone Jell 8% | 28 |
| Disperse the bentone jell under high speed cowles and add: | |
| Preparation 1 | 16 |
| Low odor mineral spirits | 85 |
| Cyclodex cobalt 6% | 3 |
| JK 270-70% | 76 |
| Water | 205 |
| Anti skin | 2 |
| Viscosity: | 80–85 KU |
| W/G: | 7.84 |
| 60° Gloss: | 85 |
| SAG: | 6 ml |

Example No. 9
O/W Paraffin Wax Emulsion

| Filtering Agent | Carrier Ingredients | Composition (% by Wt.) |
|---|---|---|
| Part A | 50% Paraffin wax | |
| | 5% SPAN 60/TWEEN 60 (50/50) | |
| | 5% Preparation 6 | |
| Part B | 40% Water | |

Method of Preparation:
1. Melt Part A ingredients together and heat to 80° C.
2. Heat Part B to 85° C.
3. Add Part B to Part A slowly with moderate agitation until inversion occurs. Add remaining water rapidly.
4. Cool in cold water bath with slow agitation to approximately 35° C.

Example No. 10
O/W Soft Microcrystalline Wax Emulsion

| Filtering Agent | Carrier Ingredients | Composition (% by Wt.) |
|---|---|---|
| Part A | 30% Microcrystalline wax (Ultraflex Amber Wax-Petrolite Corp.) | |
| | 30% SPAN 60/TWEEN 60 (78/22) | |
| | 5% Preparation 2 | |
| Part B | 62% Water | |

Method of Preparation:
1. Melt together Part A ingredients and heat to 80–90° C.
2. Heat Part B to boiling.
3. Add Part B to Part A slowly with moderate agitation until inversion occurs. Add remaining water rapidly.
4. Remove from heat and cool to room temperature without stirring.

Example No. 11
O/W Carnauba Wax Emulsion

| Filtering Agent | Carrier Ingredients | Composition (% by Wt.) |
|---|---|---|
| Part A | 10% Carnauba wax | |
| | 3% TWEEN 80 | |
| | 5% Preparation 13 | |
| Part B | 82% Water | |

Method of Preparation:
1. Melt Part A ingredients together and heat to 95° C. and hold.
2. Heat Part B to boiling.
3. Add Part B to Part A slowly with moderately fast stirring until inversion occurs. Add remaining water rapidly.
4. Remove emulsion from heat and cool rapidly with stirring.

SUNSCREEN LOTION
Example 12

| PHASE | INGREDIENTS (SUPPLIERS) | PERCENT BY WEIGHT |
|---|---|---|
| A | Petrolatum, Snow White USP (Ruger) | 35.00 |
| | Brij 721 (ICI) | 1.16 |
| | Brij 72 (ICI) | 3.86 |
| | Silicone Oil, 350 cs (Ruger) | 3.00 |
| | Preparation 9 | 5.00 |
| | Uvinul M-40 (BASF) | 3.00 |
| B | Water | 48.08 |
| | Carbopo 934 (B. F. Goodrich) | 0.40 |
| C | Sodium Hydroxide (10% Aqueous Solution) | 0.40 |
| D | Dowicil 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C. Skin protection factor was determined on three different days using ears test on rabbits a, b, & c.

| | SPF | | SPF | | SPF |
|---|---|---|---|---|---|
| a | 8.0 | a | 11.2 | a | 8.0 |
| b | 8.0 | b | 8.0 | b | 5.6 |
| c | 8.0 | c | 5.6 | c | 8.0 |
| Mean | 8.0 | | 8.3 | | 7.2 |

SUNSCREEN LOTION
Example 13

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Ruger) | 5.00 |
| | Arlasolve 200 (ICI) | 2.10 |
| | Brij 72 (ICI) | 4.90 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 65° C. Heat (B) to 70° C. Add (B) to (A) slowly with moderate agitation. Add (C). Cool to 50° C. Add (D). Cool, while stirring to 35° C. Skin protection factor was determined on rabbit ears on 3 days.

| | SPF | | SPF | | SPF |
|---|---|---|---|---|---|
| a | 11.2 | a | 4.0 | a | 4.0 |
| b | 8.0 | b | 4.0 | b | 2.8 |
| c | 8.0 | c | 4.0 | | |

SUNSCREEN LOTION
Example 13 -continued

| PHASE | INGREDIENTS (SUPPLIERS) | PERCENT BY WEIGHT | | |
|---|---|---|---|---|
| | Mean | 9.1 | 4.0 | 3.4 |

SUNSCREEN LOTION
Example 14

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Rugher) | 5.00 |
| | Arlasolve 200 (ICI) | 2.10 |
| | Brij 72 (ICI) | 4.90 |
| | Preparation 9 | 8.00 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C. Skin protection factor was determined on three rabbits on 3 days.

| | SPF | | SPF | | SPF |
|---|---|---|---|---|---|
| a | 8.0 | a | 8.0 | a | 4.0 |
| b | 8.0 | b | 8.0 | b | 4.0 |
| c | 8.0 | c | 4.0 | c | 4.0 |
| Mean | 8.0 | | 6.7 | | 4.0 |

SUNSCREEN LOTION
Example 15

| PHASE | INGREDIENTS (SUPPLIERS) | PERCENT BY WEIGHT |
|---|---|---|
| A | Petrolatum, Snow White USP (Ruger) | 35.00 |
| | Brij 721 (ICI) | 1.16 |
| | Brij 72 (ICI) | 3.86 |
| | Preparation 9 | 8.00 |
| | Silicone Oil, 350 cs (Ruger) | 3.00 |
| B | Water | 49.08 |
| | Carbopol 934 (B. F. Goodrich) | 0.40 |
| C | Sodium Hydroxide (10% Aqueous Solution) | 0.40 |
| D | Dowicil 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C. Skin protection factor was determined on rabbits on 3 days.

| | SPF | | SPF | | SPF |
|---|---|---|---|---|---|
| a | 8.0 | a | 5.6 | a | 5.6 |
| b | 8.0 | b | 11.2 | b | 4.0 |
| c | 8.0 | c | 4.0 | c | 5.6 |
| Mean | 8.0 | | 6.9 | | 5.1 |

SUNSCREEN LOTION
Example 16

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Ruger) | 5.00 |
| | Arlasolve 200 (ICI) | 2.10 |
| | Brij 72 (ICI) | 4.90 |
| | Preparation 9 | 5.50 |

SUNSCREEN LOTION
Example 16 -continued

| PHASE | INGREDIENTS (SUPPLIERS) | PERCENT BY WEIGHT |
|---|---|---|
| B | Water | 72.50 |
| | Carbopol 934 (B. F. Goodrich) | 0.20 |
| C | Sodium Hydroxide (10% Aqueous Solution) | 0.20 |
| D | Dowicil 200 (DOW) | 0.10 |

Preparation: Heat (A) to 65° C. Heat (B) to 70° C. Add (B) to (A) slowly with moderate agitation. Add (C). Cool to 50° C. Add (D). Cool, while stirring to 35° C. Skin protection factor was determined on rabbits on 4 days.

| | SPF | | SPF | | SPF | | SPF |
|---|---|---|---|---|---|---|---|
| a | 8.0 | a | 5.6 | a | 4.0 | a | 4.0 |
| b | 8.0 | b | 4.0 | b | 2.8 | b | 8.0 |
| c | 8.0 | c | 4.0 | c | 5.6 | | |
| Mean | 8.0 | | 6.4 | | 4.1 | | 6.0 |

Table of Formulas

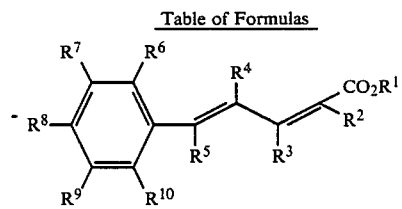

I

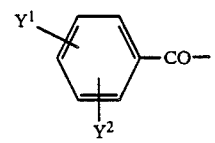

II

What is claimed is:

1. A method for protecting a plastic resin or skin of warm-blooded animal against the effects of ultraviolet radiation which comprises topically applying a composition comprising a oil, or solvent carrier having incorporated therein in an amount to provide protection against the harmful effects of ultraviolet radiation, a compound having formula I wherein $R^1$ is selected from the group consisting of an alkyl, alkenyl, alkynyl, aromatic and alkyl substituted aromatic group having up to 22 carbon atoms substituted or unsubstituted with monohydroxy or monoalkoxy groups, $R^2$ is selected from the group consisting of —H, $R^1$, —CN and aryl, $R^3$, $R^4$ and $R^5$ are selected from the group consisting of $R^1$ and H and $R^6$, $R^7$, $R^8$, $R^9$ and $R^{10}$ are independently selected from the group consisting of H, alkyl groups having 1 to 10 carbon atoms, an —$OR^{11}$ group wherein $R^{11}$ is an alkyl group having 1 to 10 carbon atoms, and where $R^8$ can also be selected from the group consisting of —$N(R^{12})_2$ wherein $R^{12}$ is H or $R^{11}$, —$COR^{11}$, $CO_2R^{11}$ or —$COCH_2COR^{11}$ and wherein $R^6$, $R^7$, $R^8$, $R^9$, $R^{10}$ may be selected from the group consisting of a hydroxyl group or a group of the formula II wherein $Y^1$ and $Y^2$ may be hydrogen, hydroxyl or methoxy wherein said formulas are:

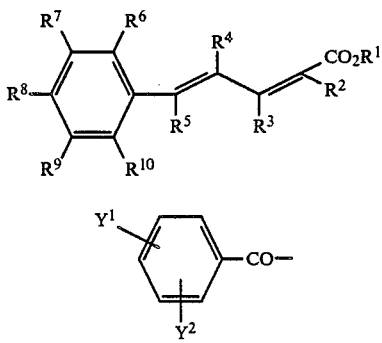

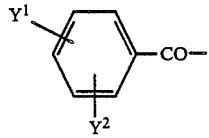

2. A method of claim 1 wherein said compound is incorporated in said composition in an amount ranging from about 0.1 to about 50% by weight.

3. A method of claim 2 wherein said compound is incorporated in said composition in an amount ranging from about 1 to about 15% by weight.

4. A method of claim 1 wherein said compound is dissolved in said carrier.

5. A method of claim 1 wherein said carrier is an aqueous emulsion.

6. A method of claim 1 wherein said substrate is the skin of a warm blooded animal.

7. A sunscreen composition comprising a cosmetically acceptable oil, or solvent carrier containing 0.5-30% by weight of a compound selected from the formula I wherein $R^1$ is selected from the group consisting of an alkyl, alkenyl, alkynyl, aromatic and alkyl substituted aromatic group having up to 22 carbon atoms substituted or unsubstituted with monohydroxy or monoalkoxy groups, $R^2$ is selected from the group consisting of —H, $R^1$, —CN and aryl, $R^3$, $R^4$ and $R^5$ are selected from the group consisting of $R^1$ and H and $R^6$, $R^7$, $R^8$, $R^9$ and $R^{10}$ are independently selected from the group consisting of H, alkyl groups having 1 to 10 carbon atoms, an —$OR^{11}$ group wherein $R^{11}$ is an alkyl group having 1 to 10 carbon atoms, and where $R^8$ can be selceted from the group consisting of —$N(R^{12})_2$ wherein $R^{12}$ is H or $R^{11}$, —$COR^{11}$, $CO_2R^{11}$ or —$COCH_2COR^{11}$ and wherein $R^6$, $R^7$, $R^8$, $R^9$, $R^{10}$ may be selected from the group consisting of a hydroxyl group or a group of the formula II wherein $Y^1$ and $Y^2$ may be hydrogen, hydroxyl or methoxy wherein said formulas are:

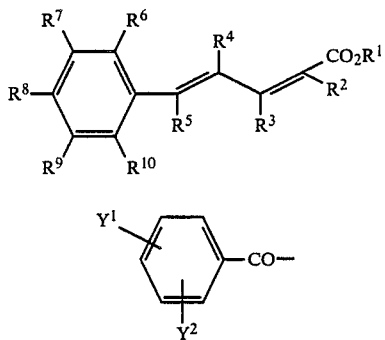

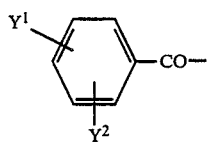

8. A composition of claim 7 wherein $R^1$ is selected from methyl, ethyl, isoamyl and ethylhexyl; $R^2$ is selected from methyl, ethyl, isobutyl and cyano groups; $R^3$, $R^4$, $R^5$ is H; $R^6$ is selected from H and oxymethyl, $R^7$ is H; $R^8$ is selected from H and oxymethyl and t-butyl and $R^9$ and $R^{10}$ are H.

9. A composition having at least one compound which absorbs radiation in the 290-320 nm range selected from Formula I of claim 7 and at least one other compound which absorbs radiation in the 320-400 nm range.

* * * * *